(12) United States Patent
Lee et al.

(10) Patent No.: US 12,622,871 B2
(45) Date of Patent: May 12, 2026

(54) DNA-BASED ELECTROCHROMIC HYDROGEL AND ELECTROCHROMIC DEVICE COMPRISING SAME

(71) Applicant: University of Seoul Industry Cooperation Foundation, Seoul (KR)

(72) Inventors: Jong Bum Lee, Seoul (KR); Hyunsu Jeon, Seoul (KR); Yong Min Kim, Seoul (KR); Hong Chul Moon, Seoul (KR)

(73) Assignee: University of Seoul Industry Cooperation Foundation, Seoul (KR)

( * ) Notice: Subject to any disclaimer, the term of this patent is extended or adjusted under 35 U.S.C. 154(b) by 706 days.

Patent file contains an affidavit/declaration under 37 CFR 1.130(b).

(21) Appl. No.: 18/075,597

(22) Filed: Dec. 6, 2022

(65) Prior Publication Data

US 2024/0180824 A1 Jun. 6, 2024

(51) Int. Cl.
| | |
|---|---|
| *A61K 9/00* | (2006.01) |
| *A61K 9/06* | (2006.01) |
| *C09K 9/02* | (2006.01) |
| *G02F 1/1503* | (2019.01) |

(52) U.S. Cl.
CPC .................. *A61K 9/06* (2013.01); *C09K 9/02* (2013.01); *G02F 1/1503* (2019.01)

(58) Field of Classification Search
CPC ............ A61K 9/06; G02F 1/1503; C09K 9/02

USPC ................................ 106/31.01, 31.13, 31.16
See application file for complete search history.

(56) References Cited

U.S. PATENT DOCUMENTS

| | | | |
|---|---|---|---|
| 2010/0189794 | A1 | 7/2010 | Luo et al. |
| 2012/0100039 | A1 | 4/2012 | Appeaning |

FOREIGN PATENT DOCUMENTS

| | | | |
|---|---|---|---|
| CN | 107764803 A | | 3/2018 |
| JP | 2012036227 A | * | 2/2012 |
| KR | 101599191 B1 | | 3/2016 |

OTHER PUBLICATIONS

Office Action issued for KR patent application Serial No. 10-2021-0151423, dated Sep. 15, 2023, with English machine translation.
Notice of Reasons for Rejection for Korean Patent Application No. 10-2021-0151423 dated 2024-05-29, with machine English translation.
Jeon, H et al. "DNA Optoelectronics: Versatile Systems for On-Demand Functional Electrochemical Applications" ACS Nano (Jan. 3, 2022) 16, 241-250.

* cited by examiner

*Primary Examiner* — James E McDonough
(74) *Attorney, Agent, or Firm* — Westman, Champlin & Koehler, P.A.; Amanda M. Prose

(57) ABSTRACT

The present disclosure relates to DNA-based electrochromic hydrogels and a device comprising the same. An electrochromic hydrogel containing DNA and a bipyridine-based compound and an electrochromic device including the same rapidly and stably change color at a low voltage and may exhibit high electrochromic efficiency.

3 Claims, 21 Drawing Sheets punching

DNA-BASED ELECTROCHROMIC HYDROGEL AND ELECTROCHROMIC DEVICE COMPRISING SAME

TECHNICAL FIELD

The present disclosure relates to DNA-based electrochromic hydrogels and an electrochromic device comprising the same. Electrochromic hydrogels and an electrochromic device comprising the same including DNA and bipyridine-based compounds may quickly and stably discolor at low voltages and exhibit high electrochromic efficiency.

BACKGROUND

DNA denatures into single strands at a temperature above a certain level, and hybridization and denaturation of DNA occur reversibly depending on the temperature. DNA has excellent reversible denaturation and biocompatibility and is studied as a material such as nanoparticles and hydrogels in the fields of tissue engineering and drug delivery.

The base pairs that make up DNA are relatively hydrophobic, so hydrophobic molecules that can interact with them can bind in major or minor grooves, or between base pairs. The hydrophobic molecule is called a DNA intercalator, and methods of fluorescently labeling DNA or inhibiting cancer cells using them have been studied. However, the study uses the function of the intercalator itself or the effect on cell division and has not been disclosed for electrochromic hydrogels and an electrochromic device comprising the same formed by combining DNA and intercalators.

(Patent Document 1) Korean Patent Registration Publication No. 10-1599191 (Feb. 24, 2016)

SUMMARY

The present disclosure provides an electrochromic hydrogel containing DNA and a bipyridine-based compound and an electrochromic device including the electrochromic hydrogel as a chromic layer.

One aspect provides an electrochromic hydrogel comprising DNA and bipyridine-based compounds.

The average molecular weight of the DNA is not particularly limited, for example, 1000 to 2 million, 5000 to 2 million, 10,000 to 2 million, 100,000 to 2 million, 500,000 to 2 million, 1 million to 2 million, 1 million to 1.5 million, or about 1.3 million.

The average base pairs of the DNA are not particularly limited, for example, 100 to 3000 bp, 500 to 3000 bp, 1000 to 3000 bp, 100 to 2500 bp, 500 to 2500 bp, 1000 to 2500 bp, or about 2000 bp.

According to one embodiment, the bipyridine-based compound may be represented by the following Chemical Formula 1.

[Chemical Formula 1]

In Chemical Formula 1, R1 and R2 may be straight chain or branched chain alkyl groups of C4 to C10, C5 to C9, or C6 to C8, respectively.

The bipyridine-based compound is a material that changes color according to the oxidation/reduction state, for example, it may be a material that is reduced and discolored when a current flows and oxidized and depigmented when the current is blocked.

The bipyridine-based compound may bind (intercalate) to DNA, and when mixed with DNA and heated above the melting temperature ($T_m$) of DNA, the DNA may be aggregated to form a hydrogel.

The bipyridine-based compound may be N,N'-alkyl-4,4'-bipyridine-based compound or Viologen. The N,N'-alkyl-4, 4'-bipyridine-based compound or viologen is, for example, dimethylviologen (N, N'-dimethyl-4,4'-bipyridinium dichloride), diethyl viologen (N,N'-diethyl-4,4'-bipyridinium dichloride), dipropyl biologen (N,N'-dipropyl-4,4'-bipyridinium dichloride), dibutyl viologen (N,N'-dibutyl-4,4'-bipyridinium dichloride), dipentyl viologen (N,N'-dipentyl-4, 4'-bipyridinium dichloride), dihexyl viologen (N,N'-dihexyl-4,4'-bipyridinium dichloride), diheptyl viologen (N,N'-diheptyl-4,4'-bipyridinium dichloride, DHV), or dibenzyl viologen (N,N'-dibenzyl-4,4'-bipyridinium dichloride, DBV).

According to one embodiment, the diethyl viologen (DEV) having two carbon numbers of the substituent did not agglomerate smoothly due to the short length of the alkyl group, and DDV (didodexyl viologen), which has 12 carbons atoms in the substituent, had an excessively long length of the alkyl group and low water solubility, making it difficult to react with DNA. In addition, DBV (dibenzyl viologen) caused an aggregation reaction with DNA, but the formed gel was not sufficiently aggregated. Therefore, in order to prepare the DNA hydrogel of the present disclosure, it is important to use a viologen substituted with an alkyl group that can be soluble in water and have sufficient binding force, bipyridine-based compounds substituted with straight or branched chain alkyl groups of C4 to C10, C5 to C9, C6 to C8 may be optimal as DNA aggregaters.

According to one embodiment, the molar ratio of the DNA base pair and the bipyridine-based compound may be 1~3:1.5~3, or 1:1.

According to one embodiment, the electrochromic hydrogel may further comprise an oxidizing species (oxidizing agent). The oxidizing species includes, for example, hypochlorous acid; hypochlorite such as sodium hypochlorite, potassium hypochlorite, and calcium hypochlorite, etc.; alkyl hypochlorite such as methyl hypochlorite, and t-butyl hypochlorite, etc.; ferrocyanide such as potassium ferrocyanide, sodium ferrocyanide, and calcium ferrocyanide, etc.; permanganate such as potassium permanganate, sodium permanganate, and calcium permanganate; etc.

Another aspect provides an electrochromic device includes a first electrode layer, a second electrode layer, and a chromic layer disposed between the first electrode layer and the second electrode layer, wherein the chromic layer including the electrochromic hydrogel.

According to one embodiment, the electrochromic hydrogel can perform both the role of an electrolyte and a discoloration material. The electrochromic device quickly and stably denaturated at a low voltage of 0.8 V and showed high electrochromic efficiency.

The first electrode layer and the second electrode layer may include at least one of Indium Tin Oxide (ITO), Indium Zinc Oxide (IZO), and Fluorine Tin Oxide (FTO).

The first electrode layer and the second electrode layer may be disposed between the first substrate and the second substrate.

The first substrate and the second substrate may be transparent substrates having a transmittance (T %) of 98% or more and may be glass or plastic.

At least one of the first electrode layer and the second electrode layer may be replaced by a metal wiring electrode or a metal wiring electrode may be further disposed on the transparent electrode. Here, the metal wiring electrode may include, for example, at least one of copper (Cu), nickel (Ni) and silver (Ag), and may be a lattice shape, a shape including a plurality of parallel wiring, or an amorphous net shape.

The thickness of the electrode layer may be 300 to 1000 nm but is not particularly limited.

Another aspect provides a method for manufacturing an electrochromic hydrogel includes preparing a solution in which DNA and a bipyridine-based compound are mixed; heating the solution the denaturation temperature of DNA to produce a shrunken DNA hydrogel; and cooling and leaving the solution to room temperature to produce a swollen DNA hydrogel.

According to one embodiment, a method for manufacturing an electrochromic hydrogel includes preparing a solution in which DNA and a bipyridine-based compound are mixed; heating the solution above the melting temperature ($T_m$) of DNA to produce a shrunken DNA hydrogel; and cooling the solution below the melting temperature of DNA to produce a swollen DNA hydrogel.

The description of the bipyridine-based compound is the same as described above.

According to one embodiment, a DNA hydrogel can be prepared by a simple method of heating an aqueous precursor solution containing DNA and diheptyl viologen above the melting temperature of DNA and cooling it back below the melting temperature, the DNA hydrogel thus prepared has stronger physical properties than other biopolymer-based hydrogels and can be easily molded into a specific shape by heating to a certain temperature or higher.

According to one embodiment, the preparation method may further include impregnating the swollen DNA hydrogel with a solution containing an oxidized species. That is, the preparation method may further include impregnating the swollen DNA hydrogel with a solution containing an oxidizing agent. The oxidizing agent is, for example, hypochlorous acid; hypochlorite such as sodium hypochlorite, potassium hypochlorite, and calcium hypochlorite, etc.; hypochlorite alkyl such as methyl hypochlorite, and hypochlorous acid t-butyl, etc.; ferrocyanide such as potassium ferrocyanide, sodium ferrocyanide, and calcium ferrocyanide, etc.; permanganate such as potassium permanganate, sodium permanganate, and calcium permanganate; etc.

The electrochromic hydrogel and an electrochromic device including the same according to one embodiment may rapidly and stably change color at a low voltage and exhibit high electrochromic efficiency.

The electrochromic hydrogel manufacturing method according to one embodiment can be produced by a simple method of heating an aqueous light bulb solution containing DNA and diheptylviologen above the melting temperature of DNA and cooling it below the melting temperature of DNA.

BRIEF DESCRIPTION OF THE DRAWINGS

FIG. 14A is a result of measuring the absorbance by voltage of the gel using UV-vis spectroscopy. FIG. 14B is a result of confirming a change in color coordinates for each applied voltage of the gel. FIG. 14C is a dynamics measurement result of the gel, showing the visible light transmittance change rate when blocked by short-circuit or open circuit. FIG. 14D is a result of measuring the electrochromic efficiency of the gel.

DETAILED DESCRIPTION

Hereinafter, one or more embodiments will be described in more detail through examples. However, these embodiments are intended to illustrate one or more embodiments illustratively, and the scope of the present invention is not limited to these embodiments.

Example 1: DNA/DHV Hydrogel Preparation and Characterization

An aqueous solution was prepared in which 12.5 mM of Deoxyribonucleic acid sodium salt from salmon testes (D1626), Sigma Aldrich (D1626) and 25 mM of Diheptyl viologen dichloride (DHV) were mixed. According to the manufacturer information of the DNA, the average number of base pairs of the DNA is about 2,000 base pairs, and the average molecular weight is 1.3 million. The molar concentration of DNA is calculated by calculating the base pairs of double-stranded DNA into one molecule, and for each base of DNA, it was mixed with the same molar concentration as DHV. That is, if the molar concentration of DNA is based on the base pair, the mole ratio of DNA to DHV is 1:2, and if the molar concentration of DNA is based on the base, the mole ratio of DNA to DHV is 1:1.

The DNA/DHV bulb aqueous solution was heated at 90° C. for 25 minutes, naturally cooled to room temperature (25° C.) and left for at least 2 hours.

Figure 1:
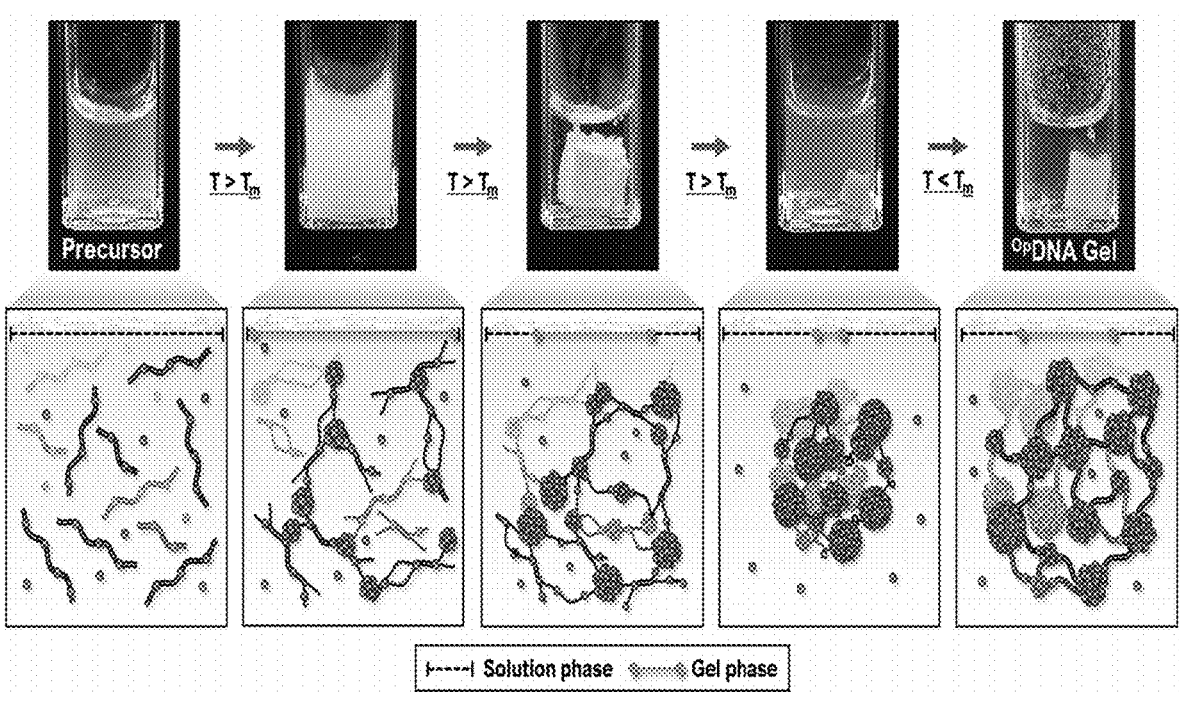
FIG. 1 shows a process of preparing a DNA/DHV hydrogel by heating an aqueous DNA/DHV bulb solution.

According to FIG. 1, the DNA/DHV bulb aqueous solution gradually became opaque in color until 6 minutes of heating and formed a DNA/DHV hydrogel in a dehydrated state after 6 minutes. When the dehydrated DNA/DHV hydrogel was naturally cooled to room temperature, it gradually absorbed water and swelled. The swelling occurred gradually over a two-hour period. The dehydrated DNA/DHV hydrogel was dark orange, but the swollen DNA/DHV hydrogel showed a light-yellow color.

The volume and rheological properties of the dehydrated or swollen state of the DNA/DHV hydrogel were analyzed.

For volume measurement, digital images of the hydrogel were taken during shrinkage and expansion that occurs when the hydrogel is synthesized in a mold having a cylindrical shape, and they were analyzed using ImageJ software.

For rheological characterization, shrunk and expanded hydrogels were analyzed using Advanced Rheometric Expansion System (ARES, Rheometric Scientific) equipment. The measurement was performed at a frequency of 0.1-100 Hz under a fixed strain of 5% by placing a 1 mm high hydrogel between parallel plates having a diameter of 8 mm.

Figure 2A:
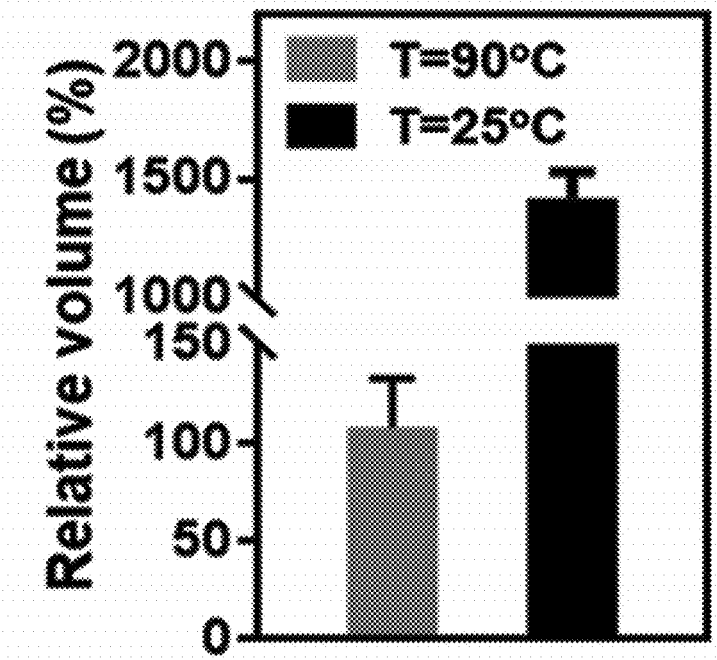
FIG. 2A and FIG. 2B shows the results of analyzing the volume (FIG. 2A) and rheological properties (FIG. 2B) of dehydrated or swollen DNA/DHV hydrogel.

According to FIG. 2A, the volume of the swollen form (25° C.) is about 10 times larger than the dehydrated (shrunk) form (90° C.).

Figure 2B:
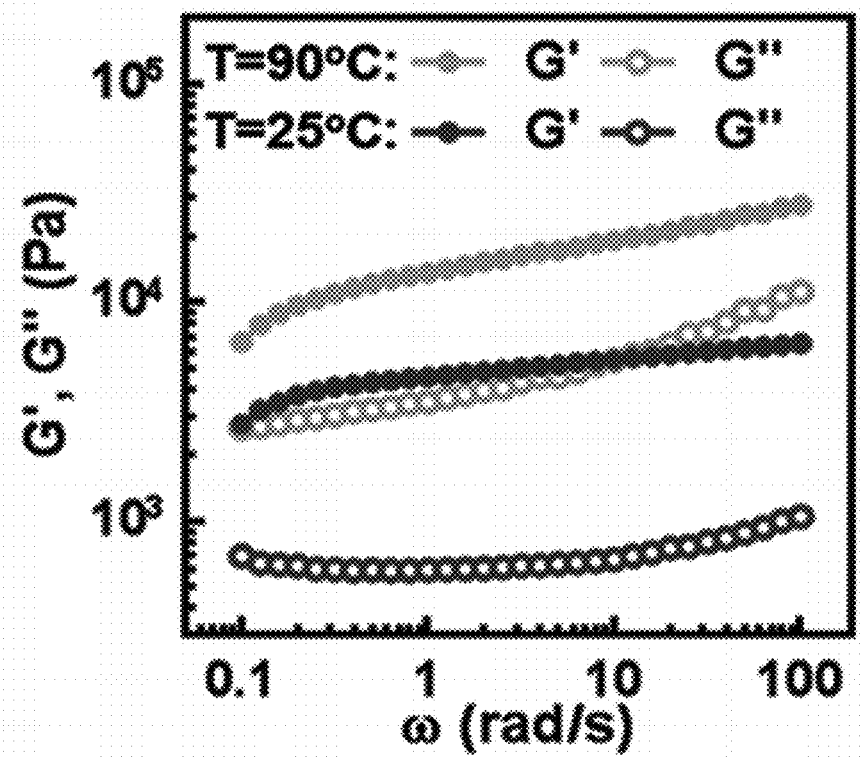

In addition, according to FIG. 2B, the DNA/DHV hydrogel showed the physical properties of the gel because the storage modulus (G') is higher than the loss modulus (G") in both the shrinkage form and the swelling form.

Surface analysis of dehydrated or swollen DNA/DHV hydrogel was performed. For surface analysis, it was cooled in an ultra-low temperature freezer to remove internal moisture while maintaining the shape of the hydrogel in a shrinking or expanding state, and then dried using a pressure reducer. SEM analysis was performed using Hitachi's SU-8010 instrument and was taken under a voltage of 1.0 kV. AFM analysis was performed using Park NX10 equipment from Park Systems and used a non-contact imaging method using NC-NCH tips.

Figure 3:
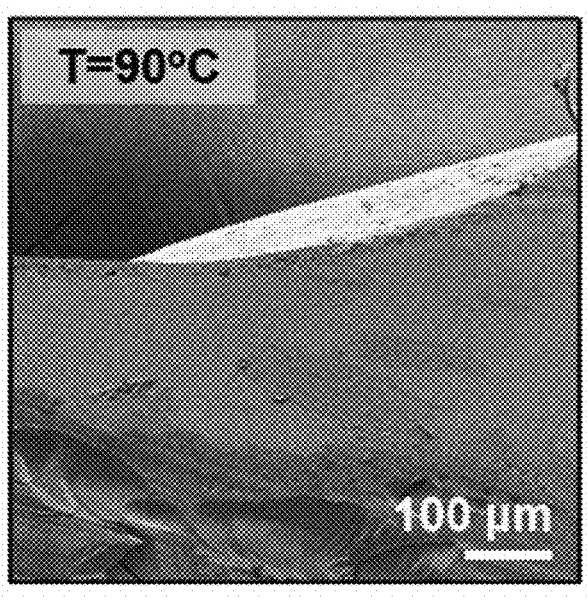
FIG. 3 shows SEM analysis results of dehydrated or swollen DNA/DHV hydrogel surfaces.
Figure 3:
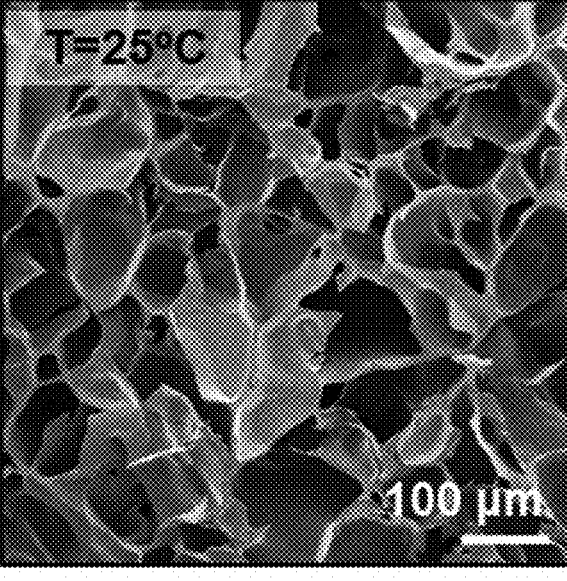

According to FIG. 3, it was confirmed that pores were formed while absorbing water in the DNA/DHV hydrogel, and that the macroscopic shape was well maintained during the shrinkage and swelling process through smooth walls (maintains the form it had in the contracted form even during swelling) in both the swelling and contraction forms.

Figure 4A:
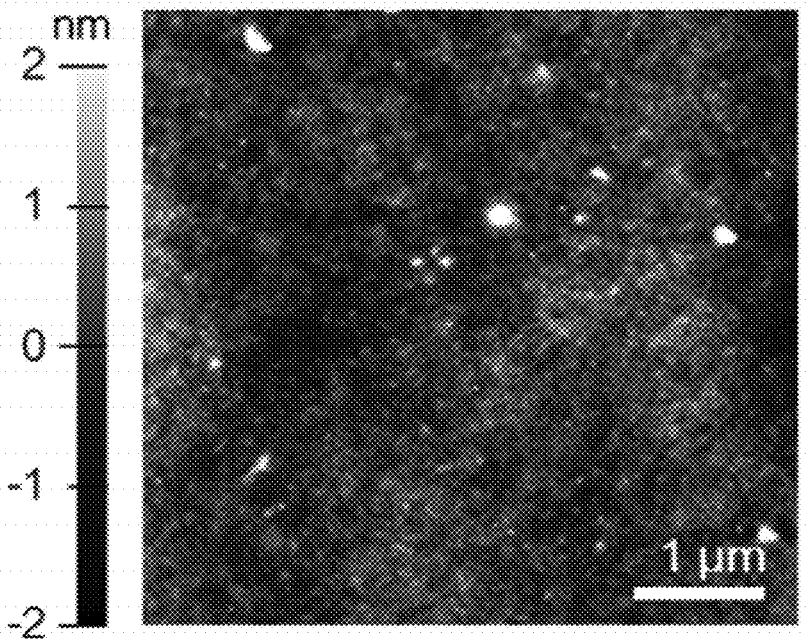
FIG. 4A and FIG. 4B show AFM analysis results of dehydrated or swollen DNA/DHV hydrogel surfaces.
Figure 4B:
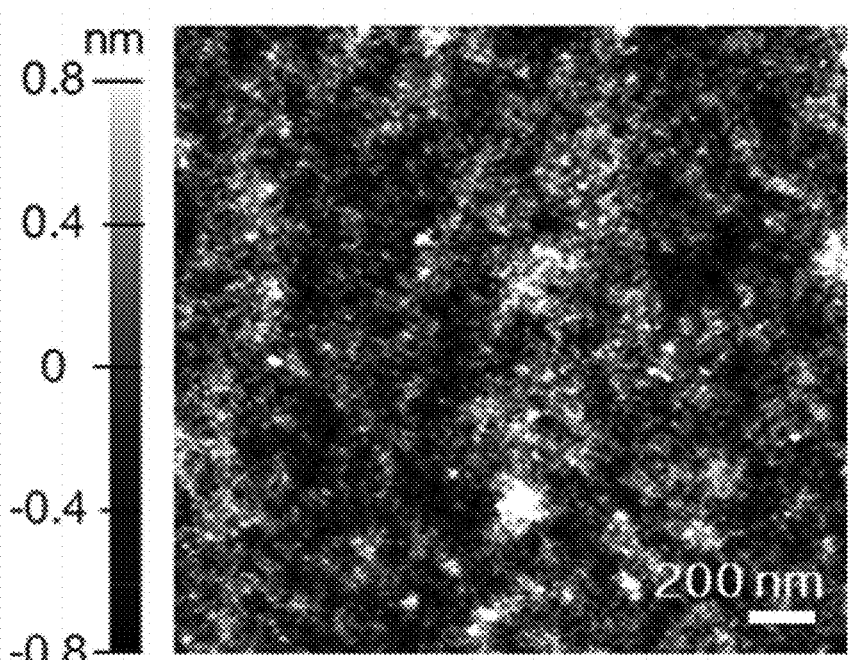

According to FIG. 4A and FIG. 4B, both the dehydration or swelling form of the DNA/DHV hydrogel showed an irregular aggregated structure on the surface, and the agglomerated structure had a height deviation of several nm, so that the surface of the DNA/DHV hydrogel was relatively smooth.

Summing up the surface structure analysis of the SEM and AFM, it can be seen that the wall formed by agglomerating DNA and DHV constitutes a hydrogel.

Example 2: Identification of the Synthesis Principle of DNA/DHV Hydrogel

In order to elucidate the principle of synthesis of DNA/DHV hydrogel, an aqueous solution of DNA at 25° C. or 90° C. and an aqueous solution of DHV were mixed and the optical density was measured.

Figure 5:
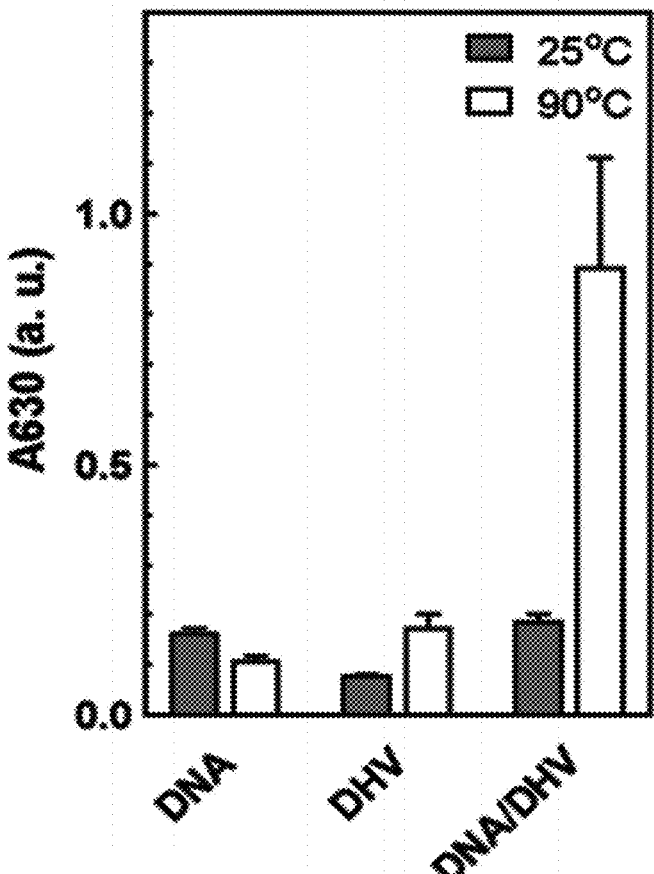
FIG. 5 shows the results of measuring optical density by mixing an aqueous DNA solution and an aqueous DHV solution of 25° C. or 90° C., respectively.

According to FIG. 5, as a result of measurements, the DNA aqueous solution and DHV aqueous solution had low optical density at both 25° C. and 90° C. In addition, the mixed aqueous solution of DNA aqueous solution at 25° C. and an aqueous solution of DHV at 25° C. also showed no change in optical density. However, the optical density of the mixed aqueous solution mixed with an aqueous DNA solution at 90° C. and an aqueous solution of DHV at 90° C. was significantly increased.

As a result of the experiment, DHV did not bind to double-stranded DNA or the degree of binding was very low, but it was combined with single-stranded DNA denatured at 90° C. to form a hydrogel.

In order to determine whether the bond of DHV and single-stranded DNA was due to a new chemical bond or by an intermolecular force, FT-IR was used to determine whether a new functional group was formed.

Figure 6:
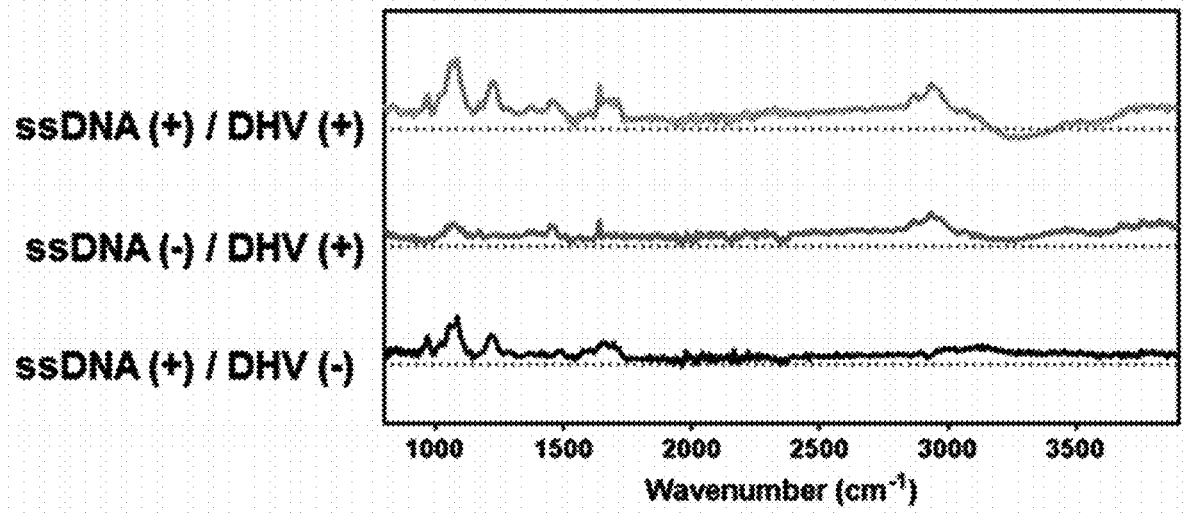
FIG. 6 shows FT-IR analysis results of single-stranded DNA, DHV, and mixed solutions thereof.

According to FIG. 6, the peaks of the mixed solution of single-stranded DNA and DHV had peaks corresponding to each of the single-stranded DNA and DHV, and no other characteristic peaks were shown. This result means that the bond of single-stranded DNA and DHV is a bond by intermolecular force.

Summing up the above experimental results, it can be seen that when an aqueous solution containing double-stranded DNA and DHV is heated above the melting temperature of DNA, DNA separated by a single strand and DHV are combined and agglomerated by intermolecular forces.

Example 3: Establishment of DNA/DHV Hydrogel Synthesis Conditions

In the process of changing the bulb aqueous solution containing DNA and DHV to gel, the content of DNA, DHV, and water contained in the aqueous solution phase and gel was confirmed.

Thermo Scientific's Nanodrop 2000c instrument was used to measure the content, and the content of each substance was calculated using the standard curves of prepared DNA and DHV.

In the same method as in Example 1 above, 12.5 mM of DNA (based on base pairs) and 25 mM of DHV were mixed and gelled at 90° C. for 25 minutes and left at room temperature for 2 hours.

Figure 7:
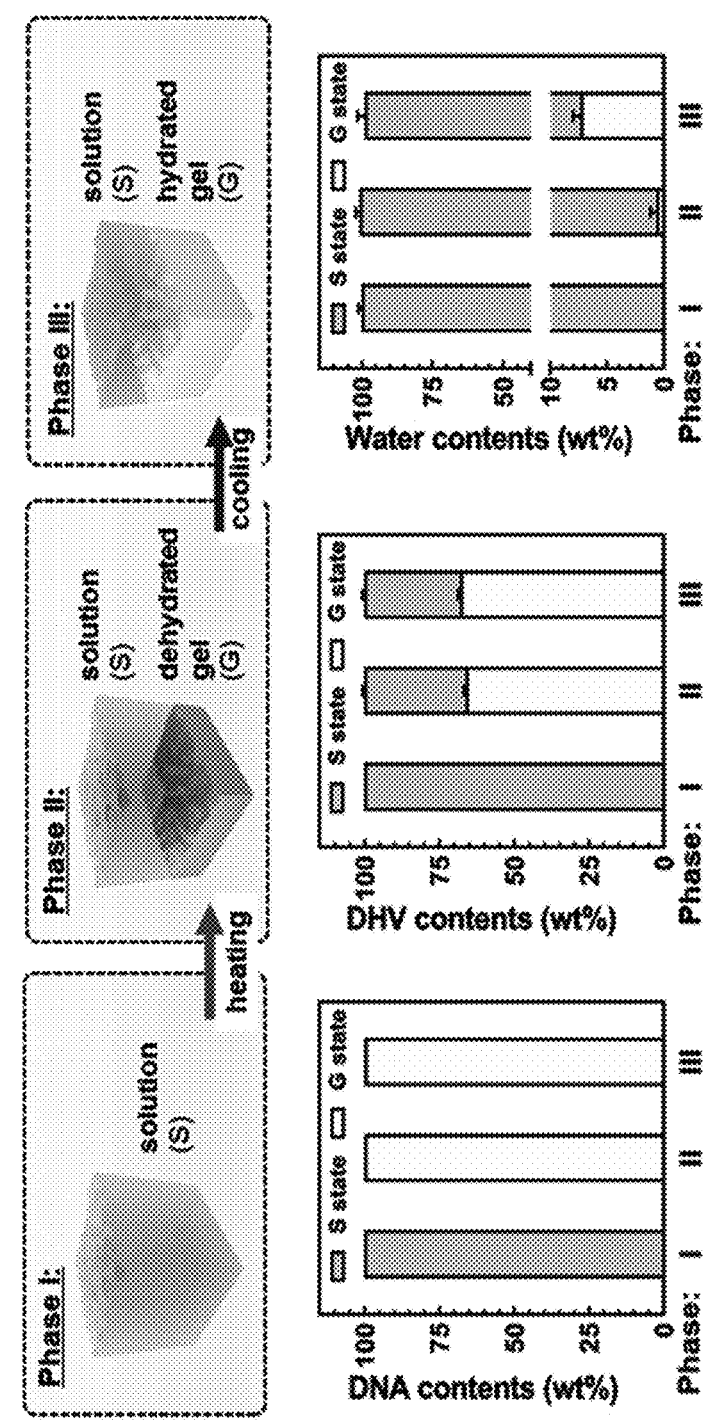
FIG. 7 shows the content of DNA, Viologen (DHV), and water contained in the solution phase and gel in the process of changing to an aqueous bulb solution, a shrunken DNA/DHV hydrogel, and a swollen DNA/DHV hydrogel.

According to FIG. 7, when the DNA/DHV gel was formed, most of the DNA was gelled. However, DHV was gelled about 70% by weight after DNA/DHV gel formation, and the remaining about 30% by weight remained in the aqueous solution. However, even if DHV remains, a gel is formed only when a sufficient amount of DHV is added, and if the ratio of DNA to DHV is added to 1:0.7, all 0.7 DHV cannot be used. Therefore, it was found that the appropriate concentration ratio of DNA and DHV for making DNA/DHV gel was 1:1 based on moles.

The concentration range of DNA and DHV required for DNA/DHV hydrogel synthesis process was confirmed. The concentration of DHV was fixed at 25 mM and the concentration of DNA was varied, or the concentration of DNA was fixed at 12.5 mM and an aqueous solution with different concentrations of DHV was prepared. And in the same way as in Example 1, the mixture was left at 90° C. for 25 minutes and at room temperature for 2 hours, and the progress of gelation was confirmed.

Figure 8A:
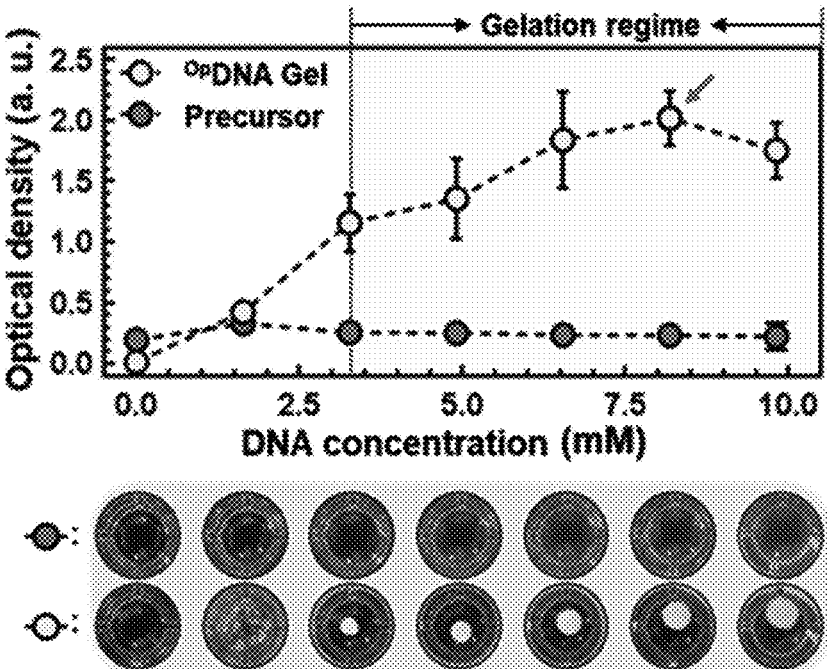
FIG. 8A and FIG. 8B is the result of confirming the gelation pattern according to the concentration of DNA (FIG. 8A) and DHV (FIG. 8B).
Figure 8B:
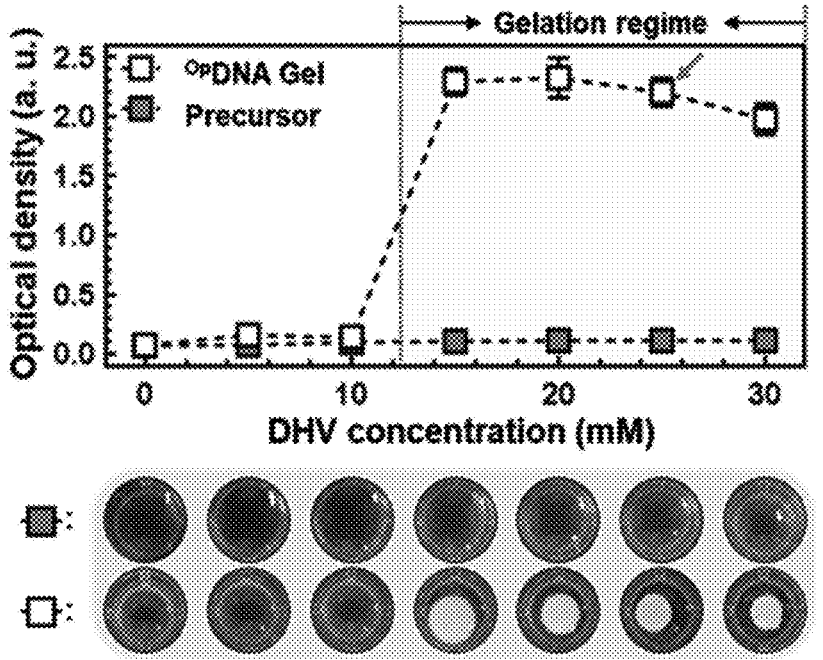

According to FIG. 8A and FIG. 8B, in the experimental group with different concentrations of DNA, an intact gel was formed when the DNA was at a concentration of 5 mM or more, but at a concentration of 2.5 mM or more but less than 5 mM, gelation was only partially carried out to obtain a broken gel. In addition, in the experimental group with different concentrations of DHV, an intact gel was formed from 15 mM to 35 mM of DHV, but gelation did not occur in the concentration range of 10 mM or less, and it existed in an aqueous light bulb solution. In addition, as a result of analyzing the optical density in the 630 nm region of the experimental group by concentration, the optical density increased in the experimental group in which gelation proceeded smoothly. Thus, it was found that at least 5 mM DNA and 15 mM or more DHV are required for the synthesis of DNA/DHV hydrogel. Thus, it can be seen that the optimal mole ratio of DNA to DHV is 1 to 3:1.5 to 3.

The maximum temperature range required to produce DNA/DHV hydrogels was confirmed. The bulb aqueous solution samples were loaded onto the PCR device, and a temperature of 44 to 95° C. was added to each sample for 2 minutes based on the maximum temperature and left at 25° C. for 30 minutes to check whether it was gelled.

Figure 9:
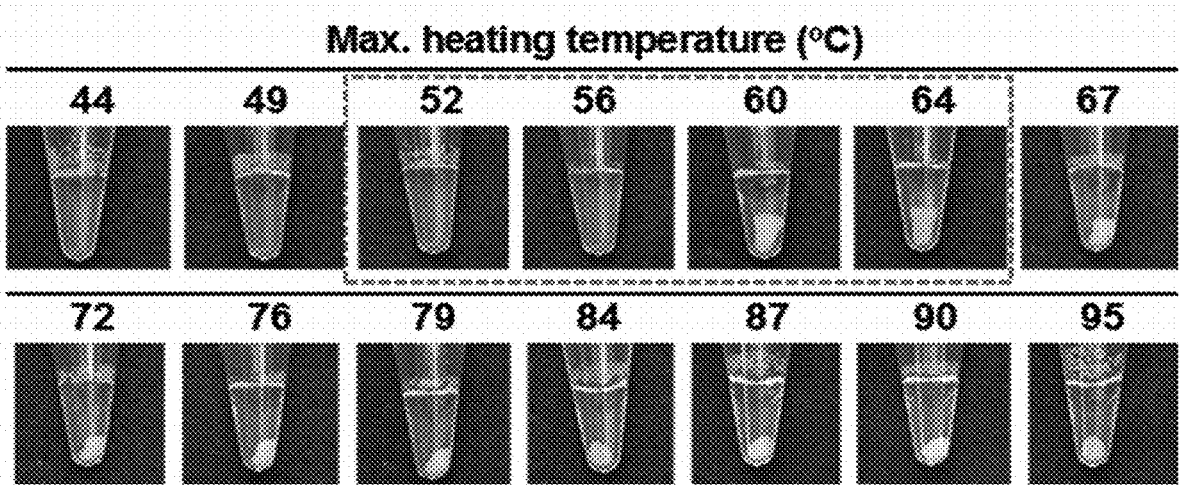
FIG. 9 is the result of preparing a DNA/DHV hydrogel by varying the maximum temperature of the heating stage of the aqueous bulb solution. The number on the tube is the maximum temperature applied to each sample.

According to FIG. 9, in order to produce a DNA/DHV hydrogel, it was confirmed that gelation occurred under conditions of about 56 to 60° C. or more. This is the melting temperature of DNA, which may vary depending on the length and sequence of DNA.

Example 4: Physical Characterization and Molding Upon DNA/DHV Hydrogel Shrinkage or Swelling For physical characterization, Mark-10's ESM303 equipment was used. The hydrogel in the shrinkage and swelling state was prepared in the form of a cuboid with a width, width of 8 mm and height of 5 mm, and tensile stress was measured under strain of 0-70% of the velocity of 3.0 N per minute.

DNA/DHV hydrogels exhibited different physical characteristics depending on temperature conditions.

Figure 10:
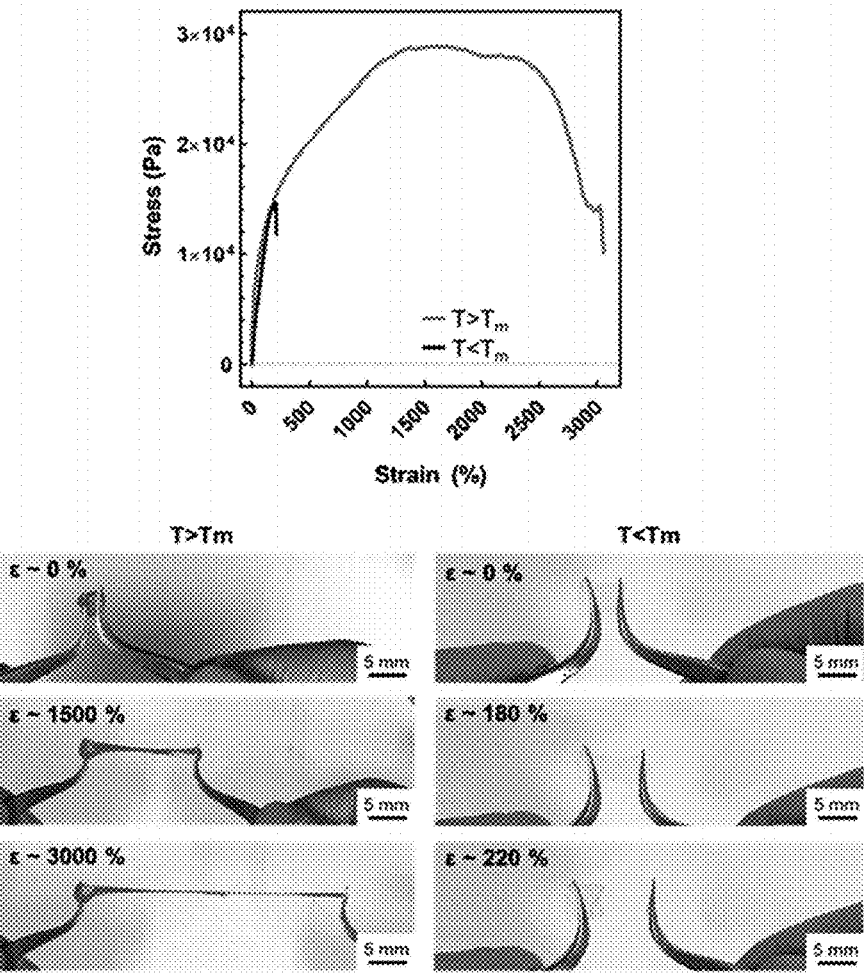
FIG. 10 is a ductility test result of a high temperature shrunken DNA/DHV hydrogel and a swollen DNA/DHV hydrogel at room temperature.

According to FIG. 10, the hydrogel (represented by T>Tm) shrunk at a high temperature (90° C.) was easily deformed in shape, stretched, and showed high adhesion properties. On the other hand, the hydrogel (represented by T<Tm) that was swollen at room temperature was not easily deformed in shape and was destroyed when a strain of about 250% or more was applied and had low adhesion properties. It is thought that the cause of this difference in physical properties is the difference from the double-stranded or single-stranded shape of DNA. DNA/DHV hydrogels in a shrinking state under high temperature conditions are in a state in which single-stranded DNA and DHV are combined, and the shape of the hydrogel is easily modified due to the short duration (tendency of polymer chains to persistence length) characteristic of single-stranded DNA, but DNA/DHV hydrogels in the swollen state are thought to maintain their shape better because double strands are formed in the state where DNA is bound to DHV, and the duration length is further increased.

Figure 11A:
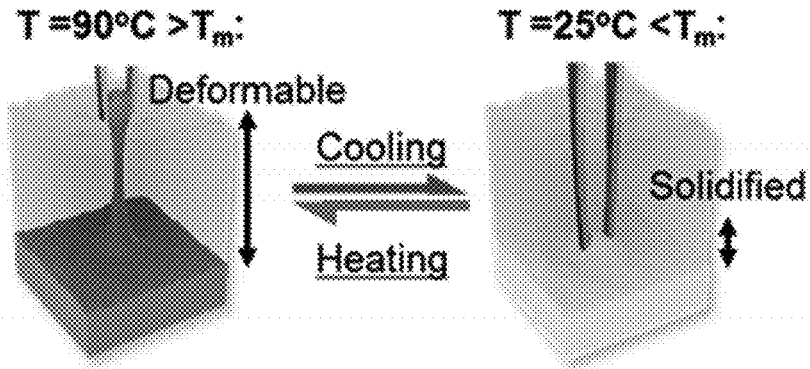
FIG. 11A and FIG. 11B show the results of confirming that shrinkage and expansion are repeated when the temperature of the DNA/DHV hydrogel is repeated at high temperature (90° C., FIG. 11A) and room temperature (25° C., FIG. 11B).
Figure 11B:
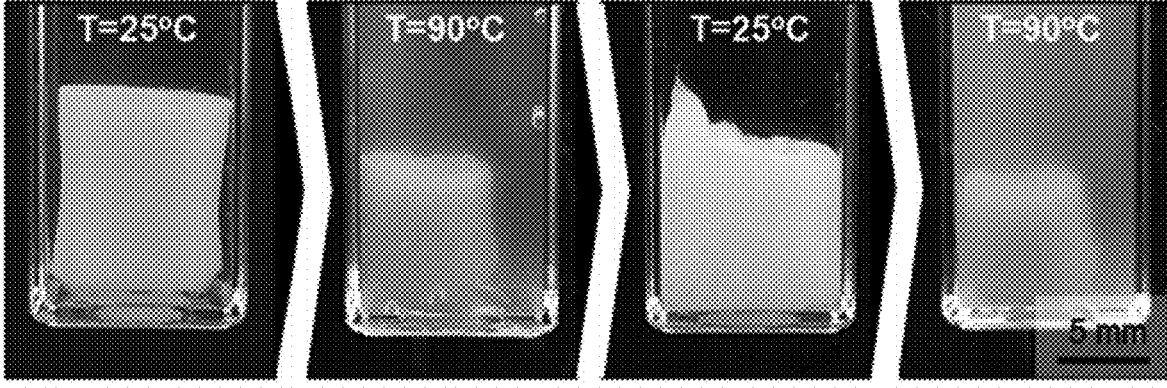

Shrinkage and swelling and physical property changes with temperature of the DNA/DHV hydrogel were reversible. According to FIG. 11A and FIG. 11B, even if the high temperature and room temperature conditions were repeated, the contraction or expansion state of the DNA/DHV hydrogel was repeated reversibly without being affected by the change in the period, and the physical properties of each state were also maintained.

DNA/DHV hydrogels can be easily shaped due to their different physical properties depending on the state of contraction or expansion.

The DNA/DHV hydrogel shrunk at high temperature was placed on a flat surface and pressed and spread thinly, and then the temperature was lowered and swollen to prepare a membrane-like DNA/DHV hydrogel.

Figure 12A:
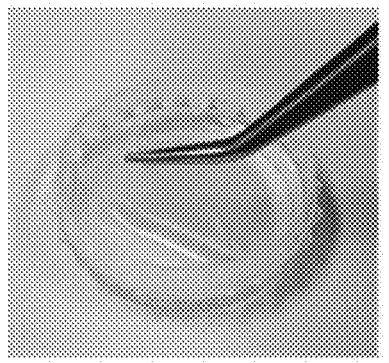
FIG. 12A and FIG. 12B show membrane and punching molding prepared by thinning and swelling the high temperature shrunk DNA/DHV hydrogel.
Figure 12B:
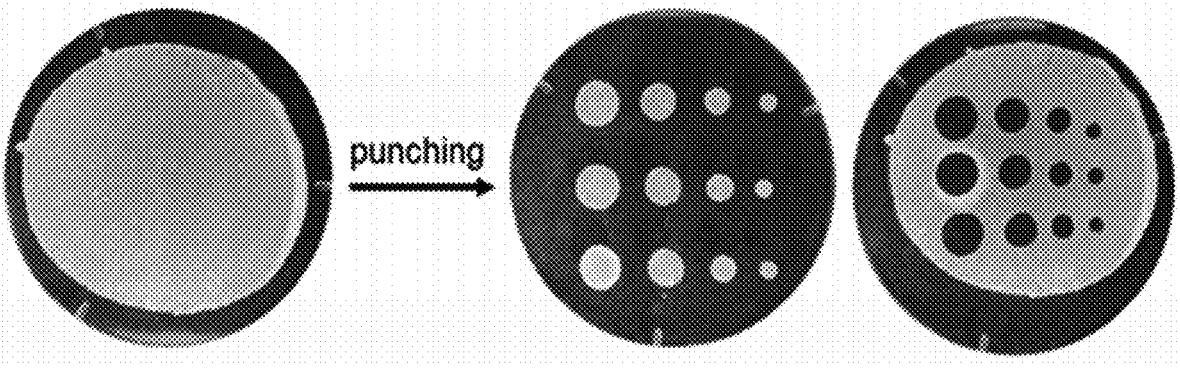

According to FIG. 12A and FIG. 12B, the membrane in which the high temperature shrinked DNA/DHV hydrogel was spread to a thickness of about 1 mm and swelled had strong physical properties that could maintain its shape outside the water and could be molded by punching and cutting.

Figure 12C:
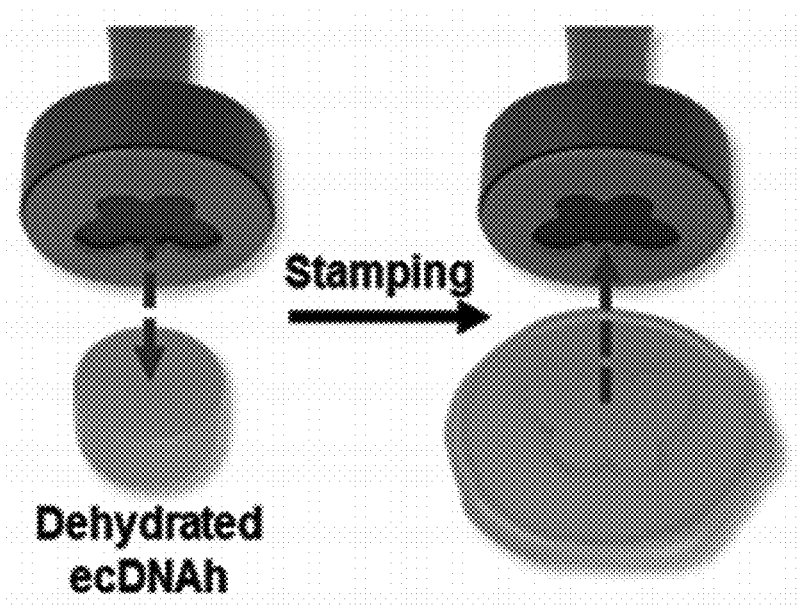
FIG. 12C and FIG. 12D show a method of stamping DNA/DHV hydrogel and molding thereby.
Figure 12D:
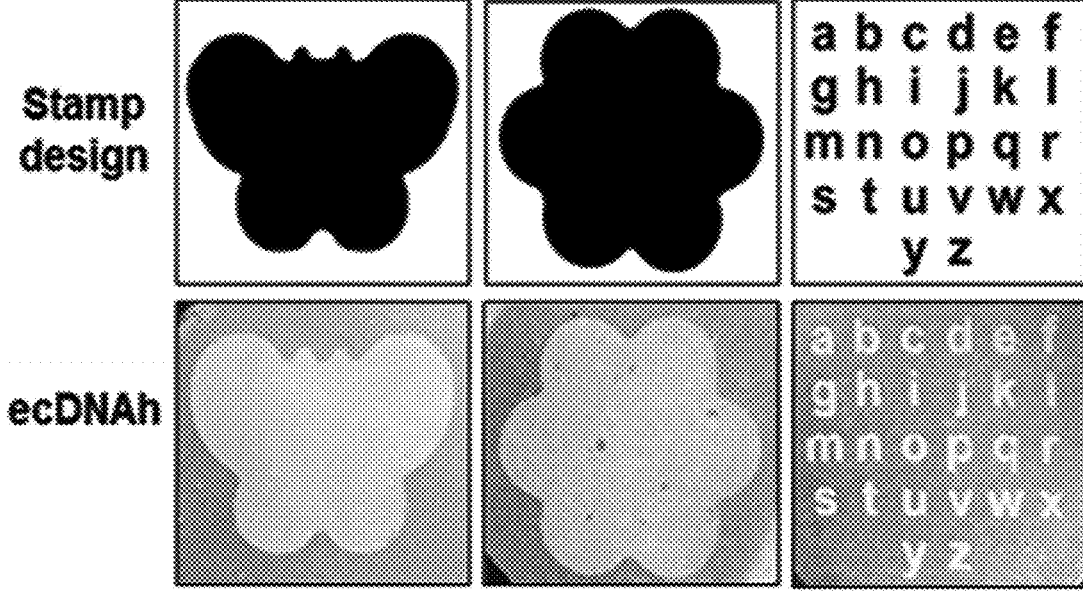

According to FIG. 12C and FIG. 12D, the hot shrinked DNA/DHV hydrogel can be stamped and molded into various shapes of intaglio or embossed, and even easily molded into complex shapes such as the English alphabet.

Figure 12E:
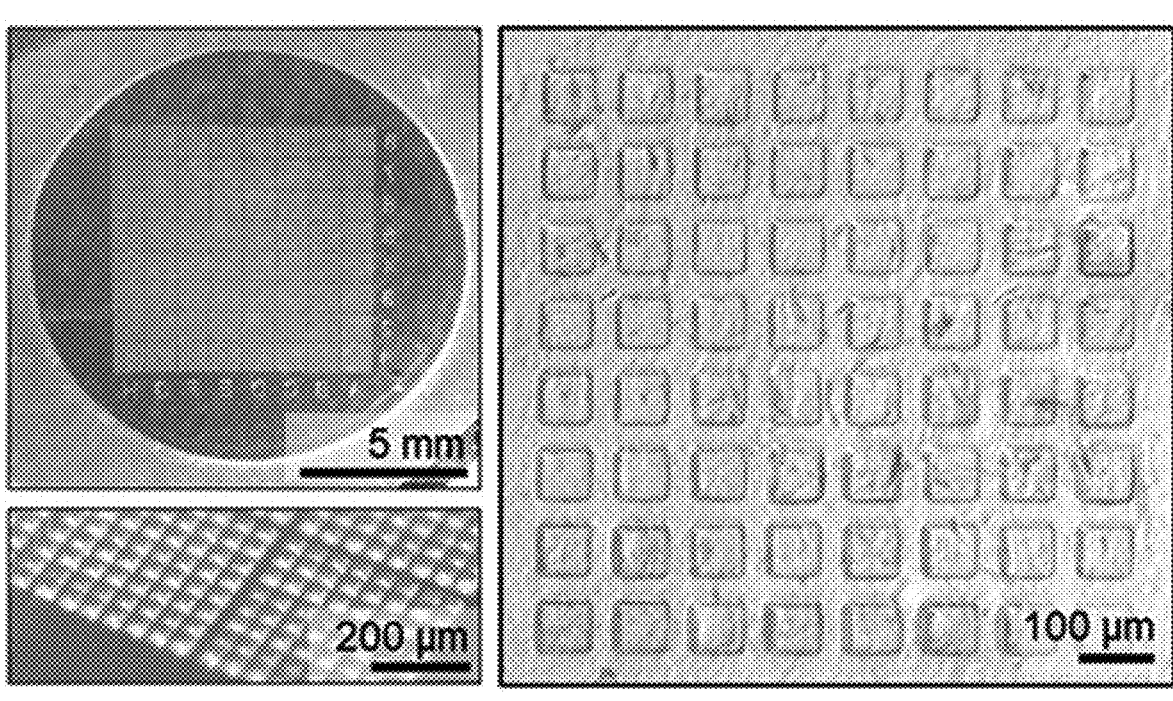
FIG. 12E shows the result of stamping DNA/Viologe hydrogel in a microwell.

According to FIG. 12E, precise stamping using microwells with each side of 50 m is possible, and a constant swelling action occurs in all directions to synthesize a DNA/DHV hydrogel in which the cubes are arranged side by side. The fact that it can be molded into microscopic forms in m is an advantage that is difficult to find in other hydrogels.

Example 5: Electrochromic Device Manufacturing Using DNA/DHV Hydrogel

In order to confirm the electrochromic properties of the DNA/DHV hydrogel, an electrochromic device combined with an ITO coated glass was manufactured and tested.

The transparent electrode used Indium Tin Oxide (ITO)-coated glass product from Asahi Glass Corporation. The transparent electrodes were treated in non-contact ultrasonic emulsifiers using acetone, isopropanol, and distilled water for 10 minutes and subjected to 10 minutes of UV/ozone treatment.

Figure 13A:
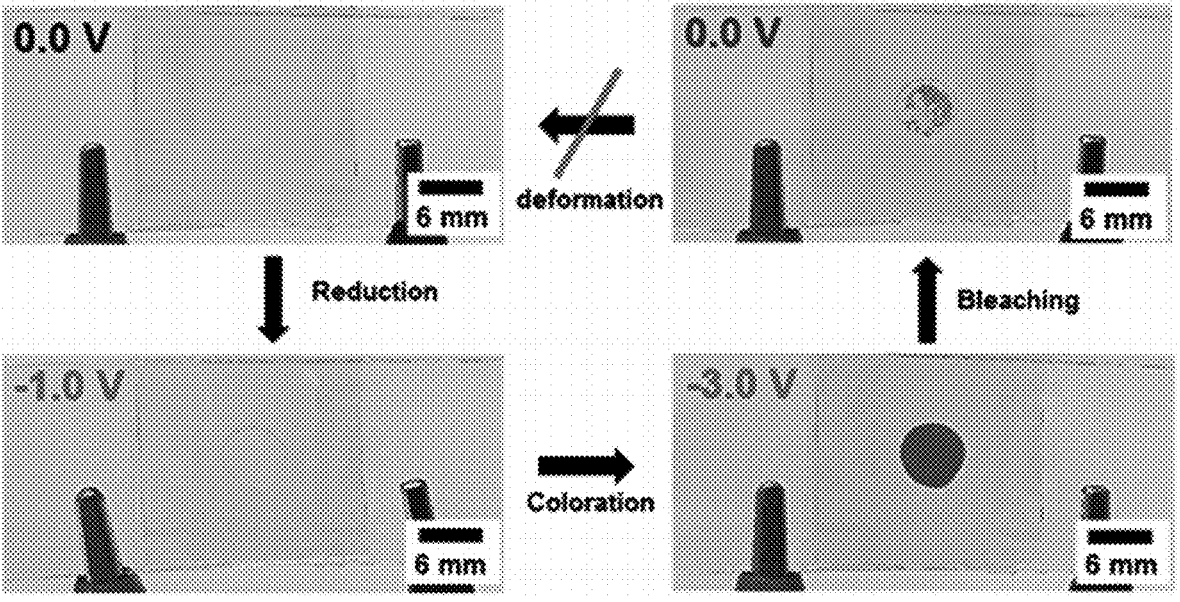
FIG. 13A shows a before and after photograph of electrochromism of a DNA/DHV hydrogel and FIG. 13B shows a method of substituting an oxidizing substance in DNA/DHV.
Figure 13B:
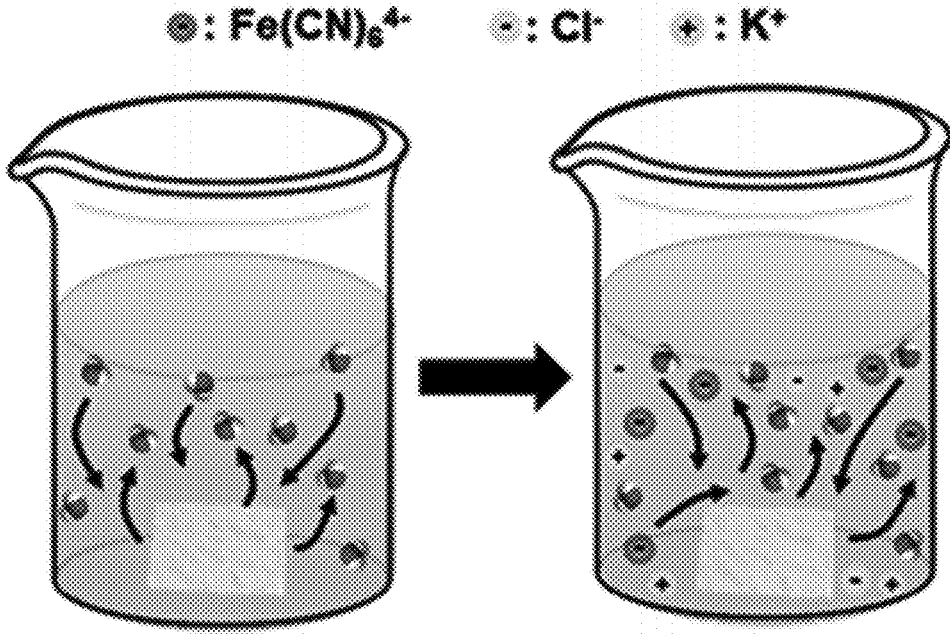

According to FIG. 13A and FIG. 13B, the electrochromic device was colored only when a voltage of −3.0 V was applied and was not completely bleached even when the voltage was cut off (0.0 V). In order to lower the voltage required for electrochromism and increase the visible light transmittance during decolorization, oxidazing species were included inside the hydrogel. DNA/DHV hydrogel was impregnated with a solution containing potassium ferrocyanide (K4Fe (CN) 6) and ion electrolyte (KCl) to allow ions to stably diffuse and enter the hydrogel.

Figure 14A:
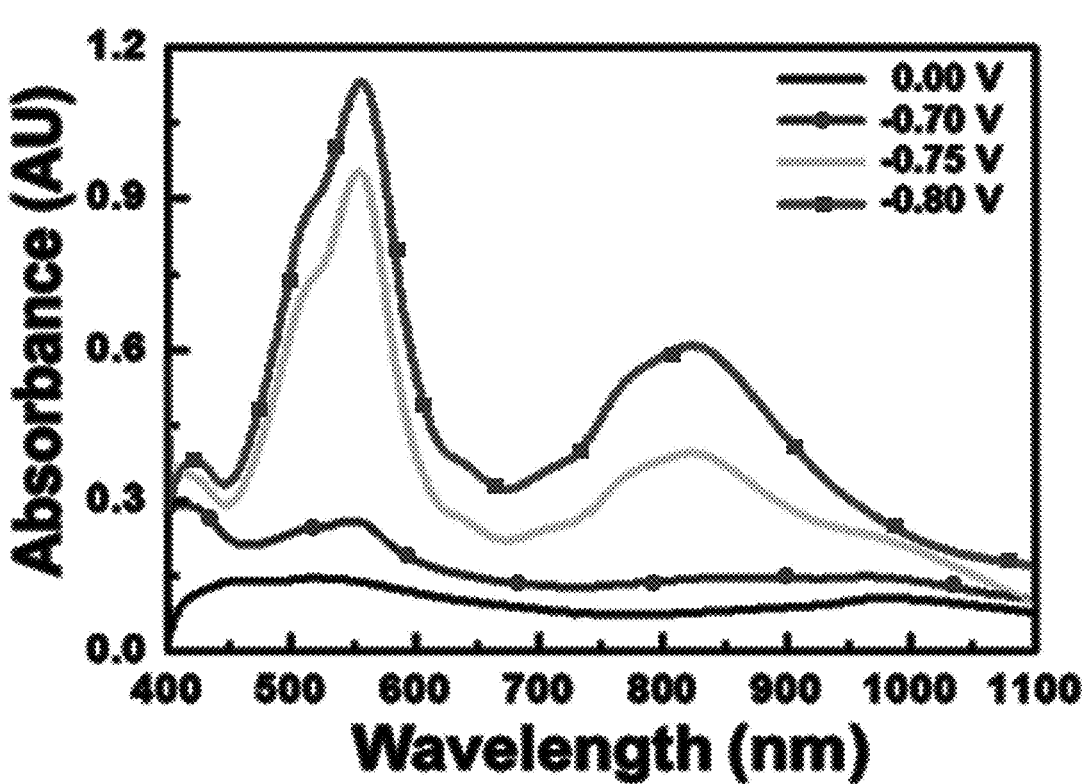
FIG. 14A through FIG. 14D show the results of electrochromic characterization of DNA/DHV hydrogel impregnated with potassium ferrocyanide.

UV-vis spectrometer was used to analyze electrochromism of DNA/DHV hydrogels impregnated with oxidized species. According to FIG. 14A, as a result of analyzing the absorbance at the entire wavelength by applying various voltages, the DNA/DHV hydrogel impregnated with oxidized species began to discolor at −0.7 V, and the voltage in which the discoloration occurred was lowered, and the strongest absorbance was shown in the 560 nm region.

Figure 14B:
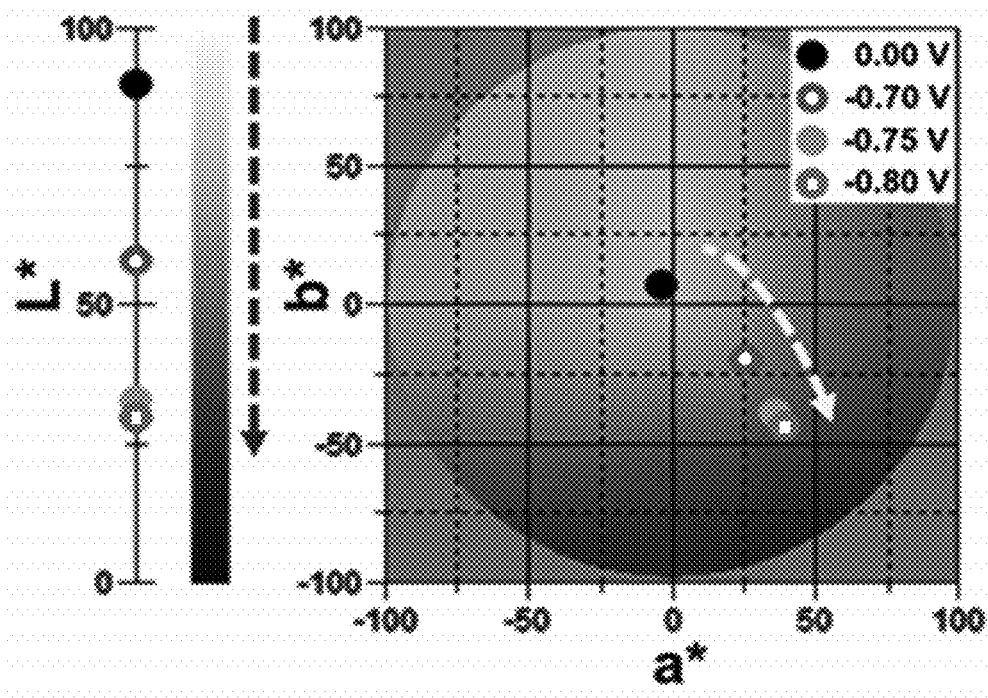

CIELAB coloration coordinates were compared to determine the color change with the magnitude of the voltage applied to the hydrogel. According to FIG. 14B, as the applied voltage increased, the luminance L* became lower and darker, a* increased to make red/violet stronger, and b* lowered to make blue more intense. Combining L*, a*, and b*, they discolored dark purple (27.9, 41.21, −43.66) as the applied voltage increased.

Hereinafter, an experiment was conducted by applying a −0.8V voltage having an absorbance of 1.0 or more.

Figure 14C:
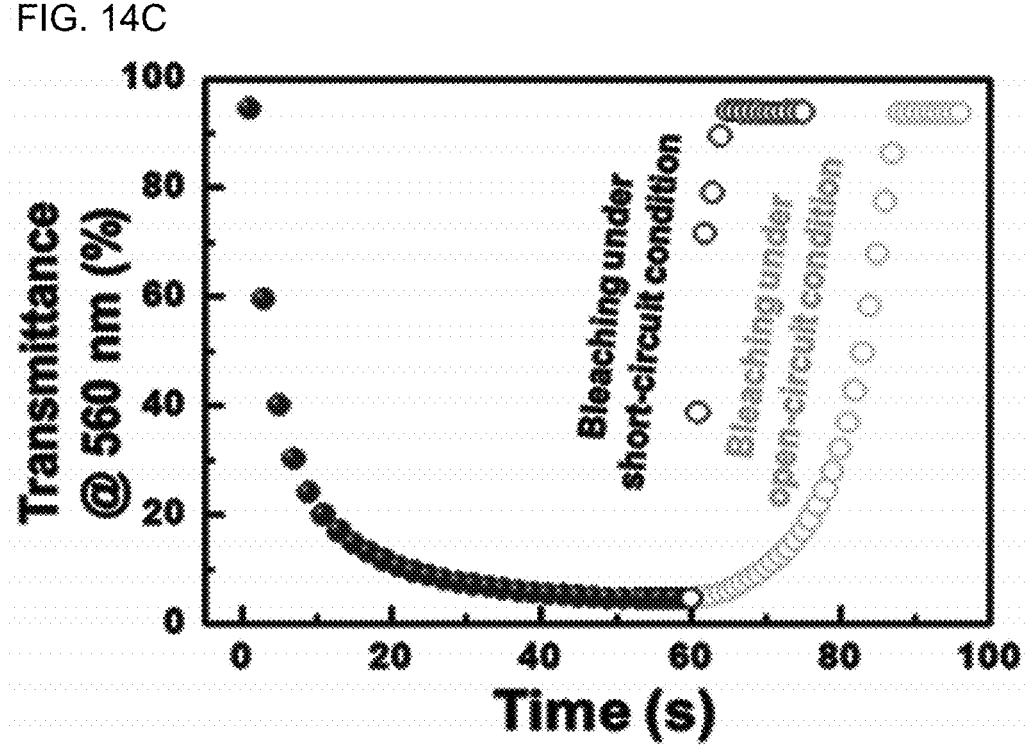

According to FIG. 14C, when electrochromic dynamics analysis of the hydrogel was performed, it took about 14 seconds for the transmittance to decrease by 90% compared to the existing when a voltage of −0.8 V was applied, and the time required to decolor (Δt 90%) by blocking the applied voltage was about 4 seconds in short-circuit and about 27 seconds in open-circuit.

Figure 14D:
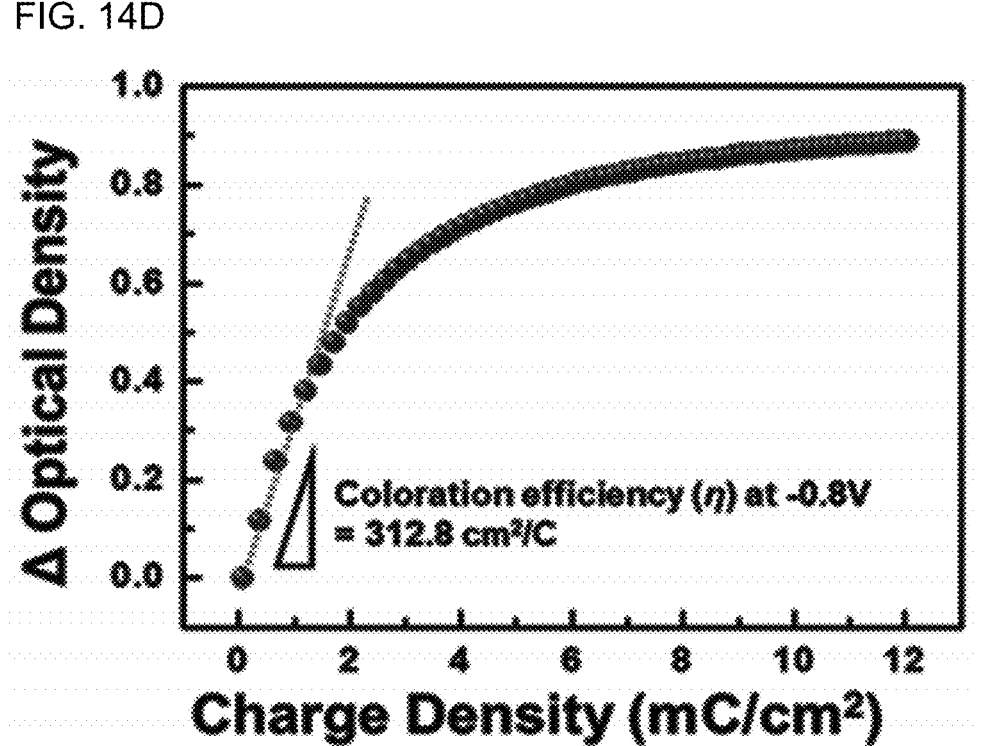

In the above experiment, the electrochromic efficiency of the hydrogel was calculated using the equation of $\eta=\Delta OD/\Delta Q=\log(Tb/Tc)/\Delta Q$. Here, $\Delta OD$, $\Delta Q$, Tb and Tc are optical density change, required charge, transmittance in the bleaching state, and transmittance in the coloring state, respectively. According to FIG. 14D, the electrochromic efficiency obtained through the above formula was 312.8 cm²/C.

According to the above test results, the DNA/DHV hydrogel impregnated with the oxidizing agent showed a very high efficiency compared to the electrochromic display using conventional DHV.

Example 6: Electrochromic Element Configuration Using DNA/DHV Hydrogel

DNA/DHV hydrogels processed in various shapes were placed between the transparent electrodes to produce electrochromic device and apply voltages.

Figure 15:
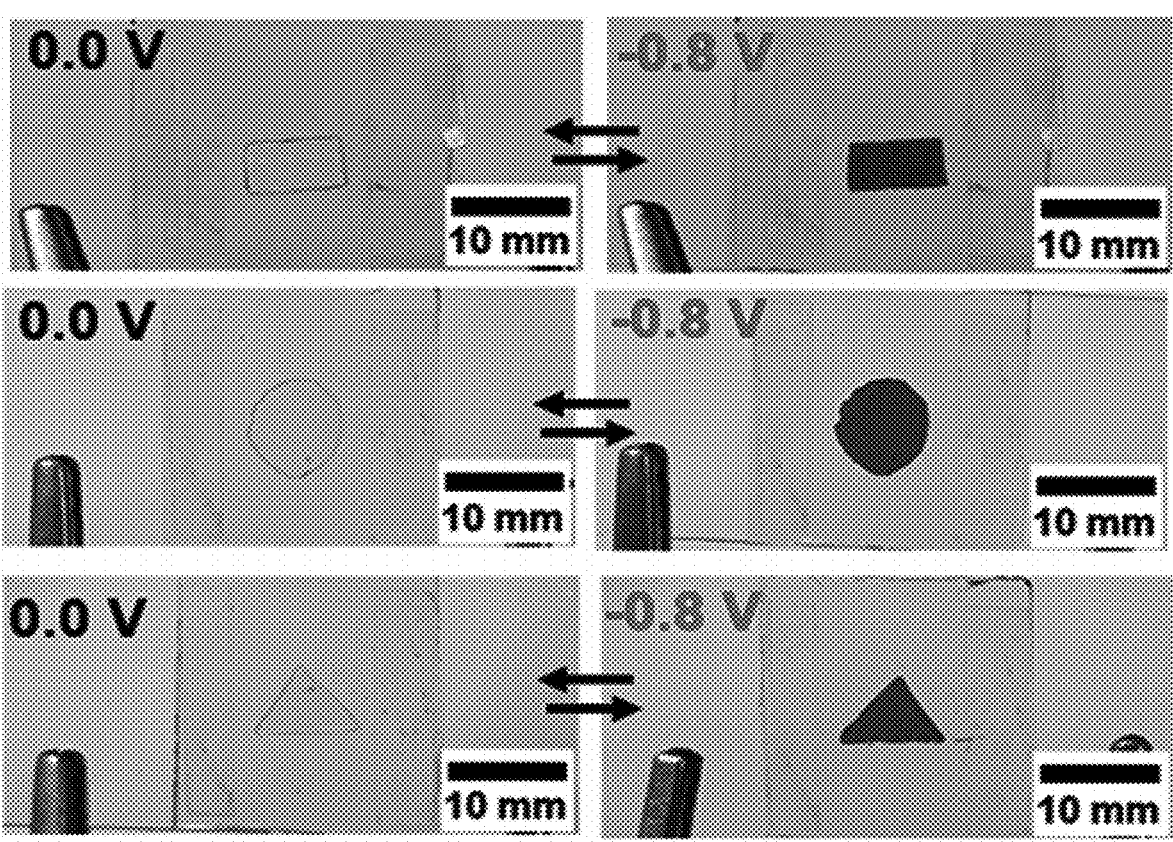
FIG. 15 is the result of discoloration by placing a DNA/DHV hydrogel-based electrochromic devices processed in various shapes between transparent electrodes and applying a voltage.

According to FIG. 15, the electrochromic device was discolored according to the form in which the DNA/DHV hydrogel was processed, such as rectangular, circular, and triangular. This indicates that the DNA/DHV hydrogel can be used for information display by patterning into a specific shape while performing a role as an electrolyte.

In the above experimental results, it was found that only the hydrogel part in contact with the negative electrode was discolored. Since the discoloration of the viologen is a phenomenon (cathodic coloration) in which electrons in the cathode part reduce the viologen, when a certain part of the hydrogel is extruded, only the protruding part in contact with the cathode can be discolored. To confirm this, the high temperature shrinked DNA/DHV hydrogel was stamped and swollen with a stamp engraved into a specific shape to synthesize a hydrogel with a specific shape protruding. The protruding shapes were (1) DNA figures, (2) uppercase letters, and (3) lowercase alphabets.

Figure 16:
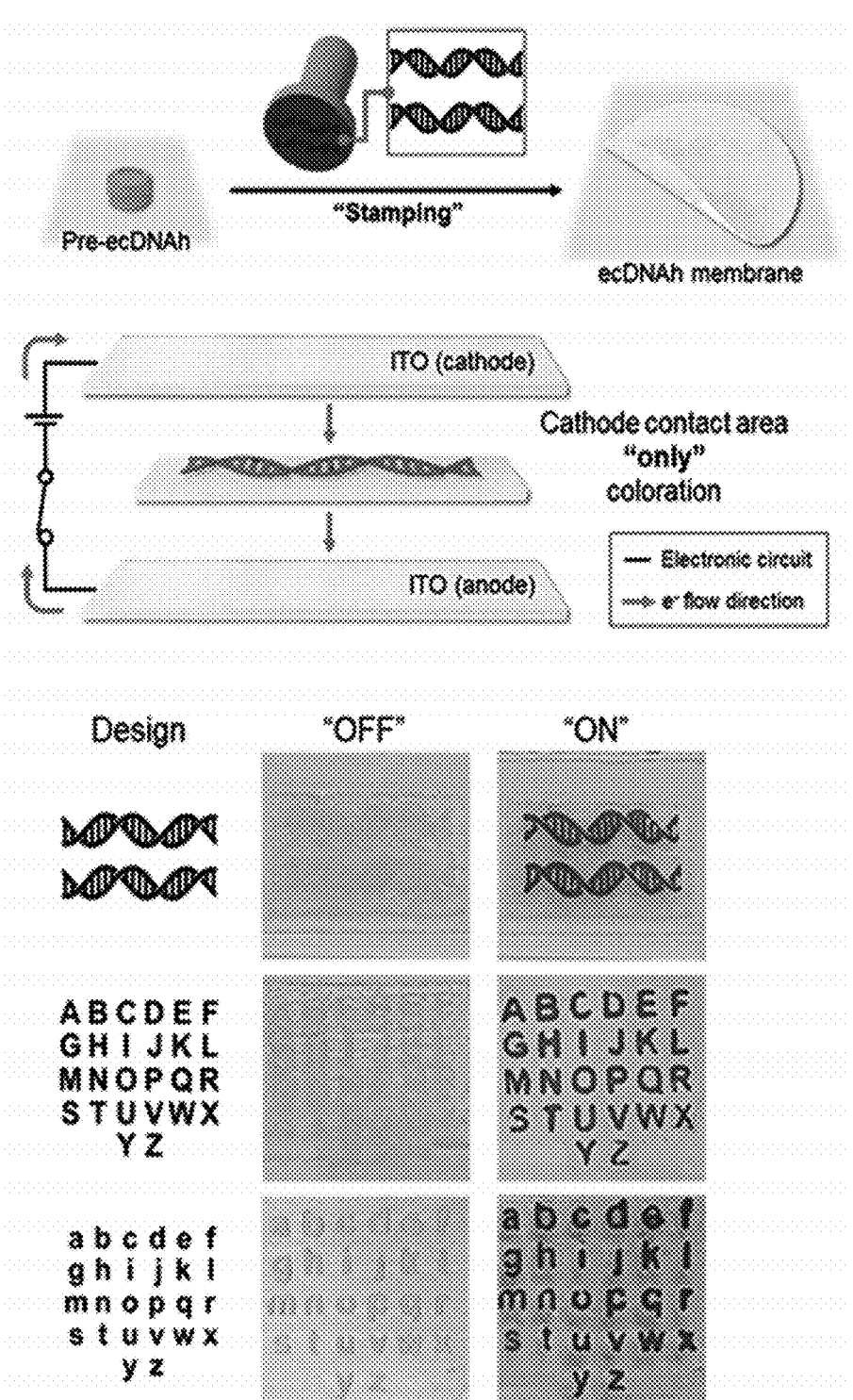
FIG. 16 shows a method of forming various types of protrusions on a DNA/DHV hydrogel by a stamping method and a result of discoloration in a desired shape.

According to FIG. 16, only the protruding site of the DNA/DHV hydrogel was in contact with the negative electrode portion and a voltage was applied, and as a result, only the protruding shape was successfully discolored. Therefore, DNA/DHV hydrogels can be utilized in high-resolution 2D electrochromic devices.

Figure 17:
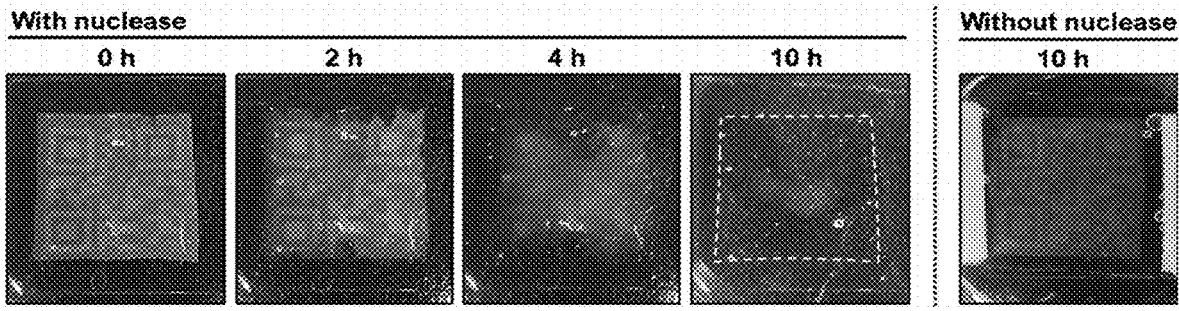
FIG. 17 shows the results of DNA/DHV hydrogel treated with DNAseI to confirm biodegradability.
Figure 18A:
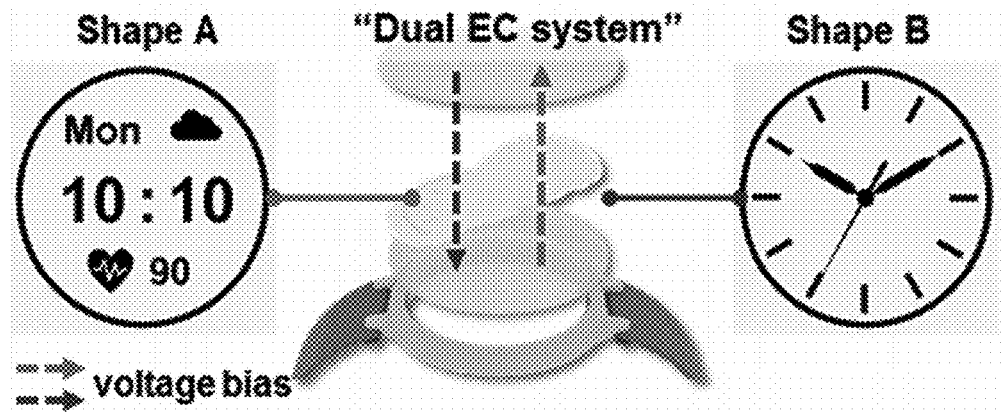
FIG. 18A and FIG. 18B show a system in which different shapes are discolored according to the direction of voltage by forming different types of protrusions on both sides of the DNA/DHV hydrogel.
Figure 18B:
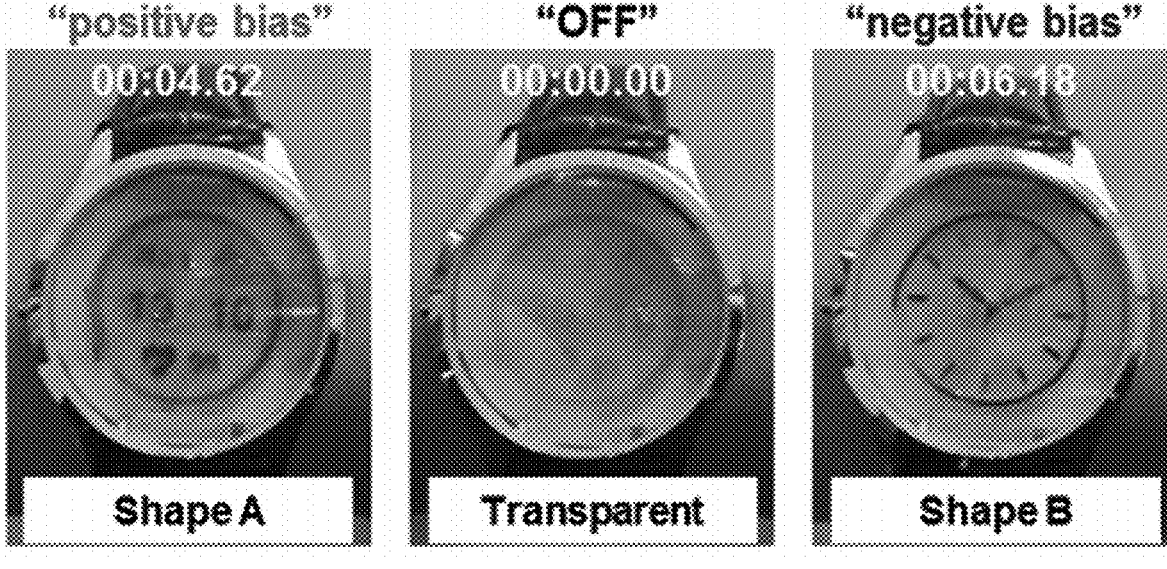

In addition, DNA/DHV hydrogels are DNA-based, so they can be biodegradable and can be used as eco-friendly electrochromizers. According to FIG. 17, DNA/DHV hydrogels treated with DNAase I were degraded within 12 hours.

Other than that, the hydrogel could be stained using fluorescent reagents such as Gelred, SYBR green I, and DAPI, which are used for fluorescently labeling DNA on DNA/DHV hydrogels, and as a result of fabricating a DNA/DHV hydrogel embossed with a QR code and applying it to a mobile phone application, the QR code was recognized (Data omitted).

Figure 19:
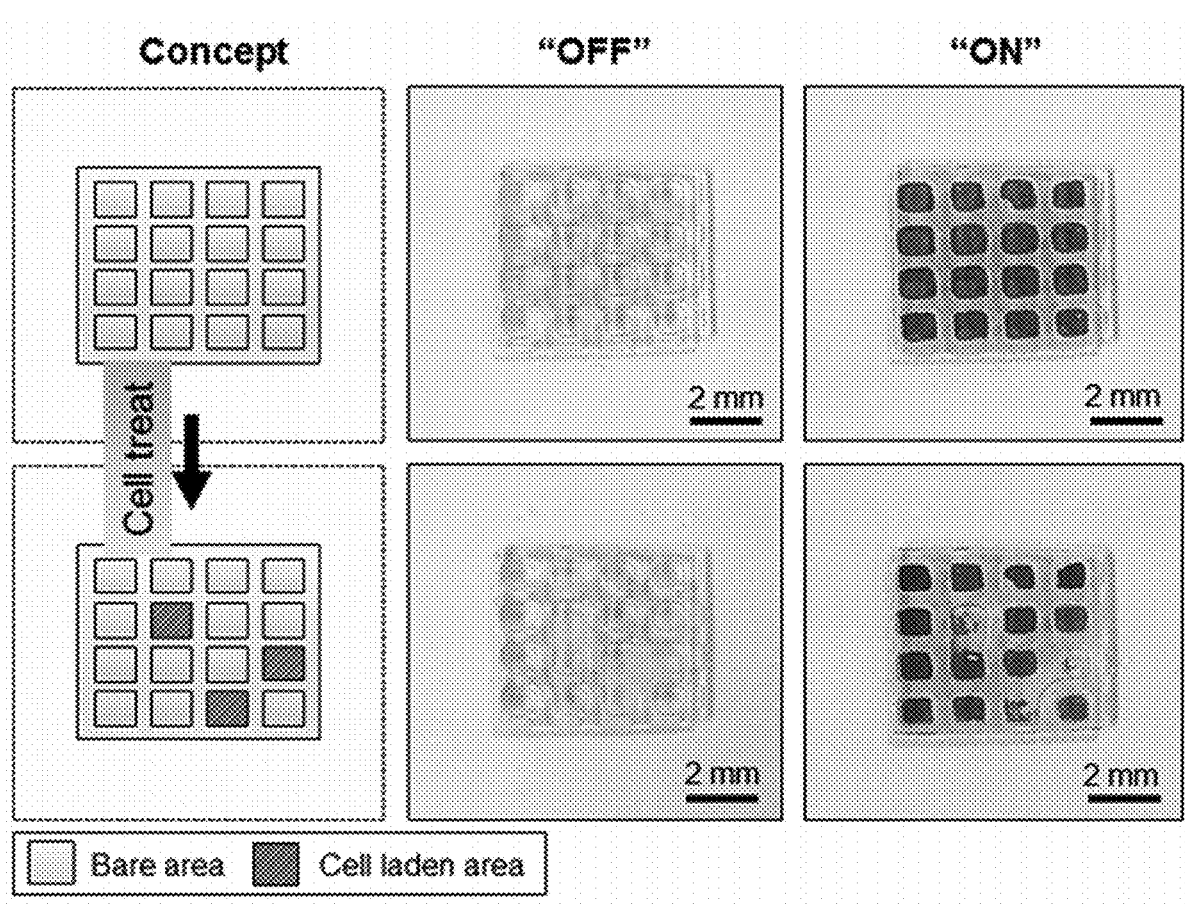
FIG. 19 shows a target kit system capable of determining the presence or absence of cells by limiting discoloration according to the presence or absence of cells.

Using the fact that only the part in direct contact with the negative electrode of DNA/DHV is discolored, different shapes were projected on both sides of the hydrogel and the direction of the voltage was changed and applied, and when the direction of the voltage was positive bias and negative bias, It was confirmed that only the part to which the cell is attached does not change (see FIG. 19). Therefore, DNA/DHV hydrogel can be used as a detection device that can detect cells.

Example 7: Selection of Optimal DNA Aggregate

Various types of biologics were used to determine whether DNA hydrogels were formed. The biologens used in the experiment were DEV (Diethyl Viologen), DDV (Didodexyl Viologen), and DBV (Dibenzyl Viologen), and the DNA and mixed wheat gel manufacturing conditions proceeded as in the above examples.

Figure 20:
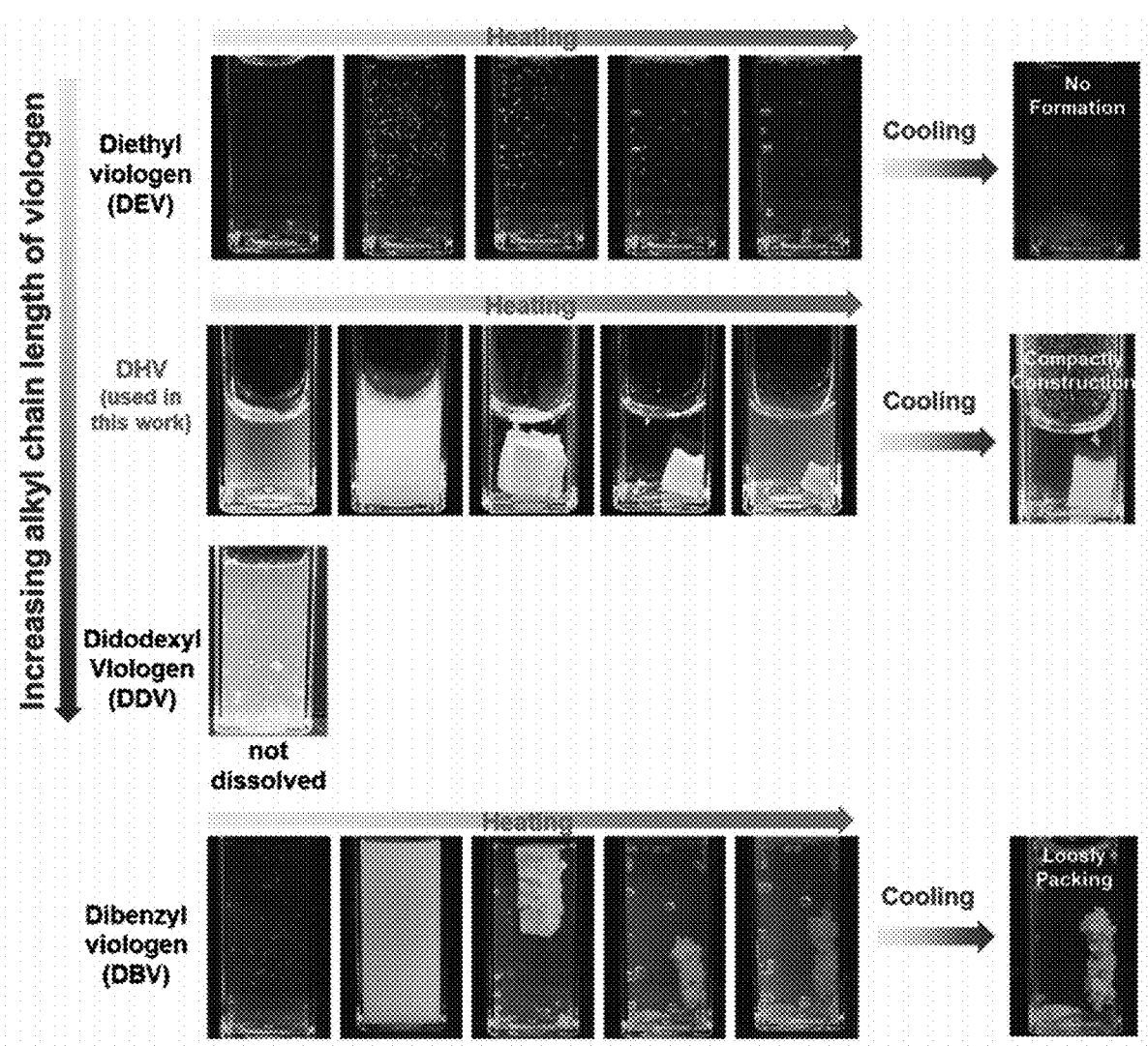
FIG. 20 shows the results of preparing a DNA hydrogel using DEV, DDV, and DBV as DNA aggregates.

According to FIG. 20, the mixed solution of DEV and DNA did not cause aggregation and gel formation even when heated. In addition, DDV had too low solubility in water, making it difficult to react with DNA. The mixed solution of DBV and DNA agglomerated when heated, but it was confirmed that gel formation did not occur smoothly because shrinkage did not occur well.

INDUSTRIAL AVAILABILITY

Therefore, according to the above experimental results, the viologen for producing DNA electrochromoin is a bipyridine having a substituent capable of strong intermolecular non-covalent bonds while being soluble in water, and at least 3 to 10 carbon It can be found that it is a bipyridine substituted with an alkyl group of at least 3 to 10.

What is claimed is:

1. An electrochromic hydrogel comprising:
a DNA and bipyridine-based compounds, and
wherein the bipyridine-based compound is represented by the following Chemical Formula 1:

[Chemical Formula 1]

$$R_1 - N^+ \text{—bipyridine—} N^+ - R_2$$

in the Chemical Formula 1, R1 and R2 are straight chain or branched chain alkyl groups of C6 to C8, respectively.

2. The method of claim 1, wherein the mole ratio of the DNA to the bipyridine-based compound is 1~3:1.5~3, and the number of moles of DNA is based on base pairs.

3. The method of claim 1, wherein the electrochromic hydrogel further comprises an oxidizing species.

\* \* \* \* \*